United States Patent
Grass et al.

(10) Patent No.: US 10,952,810 B2
(45) Date of Patent: Mar. 23, 2021

(54) METHOD AND SYSTEM FOR ADAPTIVE IMAGE GUIDED INTERVENTION

(71) Applicant: KONINKLIJKE PHILIPS N.V., Eindhoven (NL)

(72) Inventors: Michael Grass, Buchholz in der Nordheide (DE); Raymond Chan, San Diego, CA (US); Robert Manzke, Bonebuttel (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 774 days.

(21) Appl. No.: 14/411,526

(22) PCT Filed: Jul. 2, 2013

(86) PCT No.: PCT/IB2013/055416
§ 371 (c)(1),
(2) Date: Dec. 29, 2014

(87) PCT Pub. No.: WO2014/009853
PCT Pub. Date: Jan. 16, 2014

(65) Prior Publication Data
US 2015/0190205 A1    Jul. 9, 2015

Related U.S. Application Data

(60) Provisional application No. 61/669,251, filed on Jul. 9, 2012.

(51) Int. Cl.
*A61B 90/00* (2016.01)
*A61B 5/06* (2006.01)
(Continued)

(52) U.S. Cl.
CPC .............. *A61B 90/37* (2016.02); *A61B 5/065* (2013.01); *A61B 5/107* (2013.01); *A61B 5/6823* (2013.01);
(Continued)

(58) Field of Classification Search
None
See application file for complete search history.

(56) References Cited

U.S. PATENT DOCUMENTS 5,134,281 A * 7/1992 Bryenton ............. A61B 5/1073
250/227.14
6,256,090 B1 * 7/2001 Chen .................... G01V 1/3835
250/227.14
(Continued)

FOREIGN PATENT DOCUMENTS

GB      2406905 A    4/2005
WO      01/33165     5/2001
(Continued)

OTHER PUBLICATIONS

Kanellos et al., "Two dimentional polymer-embedded quasi-distributed FGB pressure sensor for biomedical applications". Optics Express, 2010 vol. 18, No. 1 (published Dec. 2009).*
(Continued)

*Primary Examiner* — Pascal M Bui Pho
*Assistant Examiner* — Yi-Shan Yang
(74) *Attorney, Agent, or Firm* — Larry Liberchuk (57) ABSTRACT

A method and system for generating imaging data during a medical intervention are provided. An external optical sensor is attached on the patient's body, and includes at least one external orientation fiber core configured to measure an orientation of the external optical sensor relative to a point of reference. The external optical sensor is interrogated to generate external sensor orientation information during the
(Continued)

medical intervention. That information is used to estimate an orientation of the external optical sensor, which is then displayed during the medical intervention.

11 Claims, 3 Drawing Sheets

(51) Int. Cl.
*G01L 1/24* (2006.01)
*A61B 5/00* (2006.01)
*A61B 5/107* (2006.01)
*A61B 34/20* (2016.01)
*A61B 5/113* (2006.01)

(52) U.S. Cl.
CPC .......... *A61B 5/6833* (2013.01); *A61B 5/6848* (2013.01); *A61B 34/20* (2016.02); *G01L 1/246* (2013.01); *A61B 5/0059* (2013.01); *A61B 5/0082* (2013.01); *A61B 5/113* (2013.01); *A61B 5/742* (2013.01); *A61B 5/7475* (2013.01); *A61B 2034/2061* (2016.02); *A61B 2034/2065* (2016.02); *A61B 2562/0266* (2013.01)

(56) References Cited

U.S. PATENT DOCUMENTS

| | | | |
|---|---|---|---|
| 6,498,652 B1* | 12/2002 | Varshneya | A61B 5/113 356/477 |
| 6,892,090 B2* | 5/2005 | Verard | A61B 34/20 600/424 |
| 2006/0004281 A1 | 1/2006 | Saracen | |
| 2006/0013523 A1* | 1/2006 | Childlers | A61B 1/00165 385/12 |
| 2006/0025677 A1* | 2/2006 | Verard | A61B 5/062 600/423 |
| 2008/0139897 A1* | 6/2008 | Ainsworth | A61B 5/0084 600/300 |
| 2008/0212082 A1* | 9/2008 | Froggatt | G01M 11/083 356/73.1 |
| 2008/0269600 A1* | 10/2008 | Csavoy | A61B 90/17 600/426 |
| 2008/0286155 A1* | 11/2008 | Kane | G01N 21/77 422/82.08 |
| 2009/0088629 A1 | 4/2009 | Groszmann et al. | |
| 2009/0137952 A1* | 5/2009 | Ramamurthy | A61B 5/06 604/95.01 |
| 2009/0185772 A1* | 7/2009 | Xia | A61B 5/0059 385/13 |
| 2009/0226069 A1* | 9/2009 | Razzaque | G06K 9/3216 382/131 |
| 2009/0227877 A1* | 9/2009 | Tran | A61B 5/021 600/483 |
| 2010/0160771 A1* | 6/2010 | Gielen | A61B 34/20 600/424 |
| 2010/0313668 A1* | 12/2010 | Tao | G01B 11/16 73/800 |
| 2011/0202069 A1 | 8/2011 | Prisco et al. | |
| 2011/0263950 A1* | 10/2011 | Larson | A61B 5/1113 600/301 |
| 2011/0302694 A1* | 12/2011 | Wang | A61B 5/103 2/160 |
| 2013/0131499 A1 | 5/2013 | Chan et al. | |
| 2013/0188855 A1 | 7/2013 | Desjardins et al. | |
| 2013/0211261 A1 | 8/2013 | Wang et al. | |
| 2013/0216025 A1 | 8/2013 | Chan et al. | |
| 2014/0088377 A1 | 3/2014 | Manzke et al. | |
| 2014/0155737 A1 | 6/2014 | Manzke et al. | |

FOREIGN PATENT DOCUMENTS

| | | |
|---|---|---|
| WO | 2011098926 A1 | 8/2011 |
| WO | 2011138691 A1 | 11/2011 |
| WO | 2011141830 A1 | 11/2011 |
| WO | 2013057703 A1 | 4/2013 |

OTHER PUBLICATIONS

Nishiyama et al, "A deformation sensitive pad-structure embedded with hetero-core optic fiber sensors". Sensors and Actuators A 136 (2007) 205-211.*

De jonckheere et al., "OFSETH: Smart medical textile for continuous monitoring of respiratory motions under magnetic resonance imaging", IEEE EMBS, 2009.*

Nishiyama et al., "Wearable sensing glove with embedded hetero-core fiber-optic nerves for unconstrained hand motion capture". IEEE, 2009, vol. 58, No. 12, pp. 3995-4000.*

* cited by examiner

METHOD AND SYSTEM FOR ADAPTIVE IMAGE GUIDED INTERVENTION

CROSS REFERENCE TO RELATED APPLICATIONS

This application is a national filing of PCT application Serial No. PCT/IB2013/055416, filed Jul. 2, 2013, published as WO 2014/009853 A2 on Jan. 16, 2014, which claims the benefit of U.S. provisional application Ser. No. 61/669,251 filed Jul. 9, 2012, which is incorporated herein by reference.

The present application relates generally to a method and system for the medical imaging arts, and in particular to adaptive image guided medical intervention. An "intervention" in this context is the insertion of one or more medical instruments into a patient in order to perform a medical procedure. The medical instrument may be, for example, a needle, a mechanical scalpel (lancet), a laser scalpel, an endoscope, a microscopic imaging probe, a surgical stapler, a refractor, a cautery device (electrical or optical), a catheter, a chisel, a clamp, a probe, a trocar, scissors, or the like. In many intervention procedures, a physician will use more than one medical instrument.

Such medical interventions are often performed in conjunction with pre-operative and/or intra-operative imaging scans of the patient, to guide instrument manipulation during the procedure. Pre-operative or scout volumetric imaging performed with modalities such as Computed Tomography (CT), Magnetic Resonance Imaging (MRI), ultrasound, fluoroscopy and the like can be used to identify the locations of tissue targets prior to an intervention. The pre-operative imaging scans can further be used to identify sensitive tissues surrounding the targets in order to minimize complications resulting from collateral tissue damage. Intra-operative imaging volumes, by contrast, are acquired in real-time to monitor the intervention while the procedure is taking place. An intra-operative imaging scan may employ the same or a different imaging modality as the pre-operative imaging scan. In one example, CT imaging may be used for pre-operative imaging, and ultrasound imaging may be used for real-time image guidance.

In another example, CT imaging may be used for pre-operative imaging, and more CT imaging may be used for intra-operative image guidance. Such imaging is performed for many different kinds of interventional procedures, such as for example radiofrequency ablations of liver tumors, abdominal drainages, and biopsies. The pre-operative CT imaging data may be used to plan the intervention procedure. The intra-operative CT imaging data may be used to check the position of the medical instrument on its way from the patient's body surface to the target region within the patient's body. Intra-operative CT imaging may also be used to assess patient motion and organ deformation(s) due to instrument insertion and manipulation during the procedure. However, repeating imaging scans during the intervention procedure undesirably increases the radiation dosage delivered to the patient and/or the medical professionals performing the intervention, and also slows the progress of the intervention. Therefore, there is a need in the art for an intra-operative imaging procedure which reduces the number of imaging scans while maintaining navigation accuracy.

The present disclosure proposes an optical shape sensing based method for performing intra-operative imaging procedures. During the imaging procedure, a patch is affixed to the patient's body at the insertion site and/or in proximity to the target anatomy of interest. The patch has an optical shape sensing fiber interwoven or otherwise embedded into the patch. Fiber Optic Shape Sensing and Localization (FOSSL) tracking technology tracks the spatial orientation of the optical wire. The "orientation" of an optical wire as specially defined herein corresponds to identifying a shape and a position of the optical wire relative to a designated reference point. This is accomplished for example via a plurality of sensors placed along the length of the optical fiber to measure deflections and bending of the optical fiber. Such FOSSL tracking technology is generally described, for example, in the following three patent applications:

- WO 2011/098926, to inventors R. Chan, G. Shechter, A. E. Desjardins, G. 'T Hooft, and C. S. Hall, entitled "Apparatus, System and Method for Imaging and Treatment Using Optical Position Sensing", filed on Jan. 14, 2011 and designating the United States, claiming priority to U.S. Provisional Patent Application Ser. No. 61/302,571, filed on Feb. 9, 2010;
- WO 2011/138691, to inventors J. Wang, R. Chan, G. 'T Hooft, A. E. Desjardins, and C. S. Hall, entitled "Motion Compensation and Patient Feedback in Medical Imaging Systems", filed on Mar. 29, 2011 and designating the United States, claiming priority to U.S. Provisional Patent Application Ser. No. 61/332,212, filed on May 7, 2010; and
- U.S. Provisional Patent Application Ser. No. 61/514,585, to inventors R. Manzke, G. 'T Hooft, R. Chan, and A. E. Desjardins, entitled "Dynamic Constraining with Optical Shape Sensing", filed on Aug. 3, 2011.

The present application incorporates those three prior applications herein by reference for their respective disclosures of FOSSL tracking technologies and methods. Thus, optical shape sensing utilizes one or more optical fibers which are integrated into the patch and perhaps also with the inserted medical instrument, and connected to an analysis unit outside of the patient's body. The position and the shape of the optical fiber core(s) are measured in real time using modeling and analysis of the optical signal returned from each of the fiber cores with respect to the external analysis unit.

The method comprises generating imaging data during a medical intervention performed on a patient. An external optical sensor is attached on the patient's body, and includes at least one external orientation fiber core configured to measure an orientation of the external optical sensor relative to a point of reference. The external optical sensor is interrogated to generate external sensor orientation information during the medical intervention. That information is used to estimate an orientation of the external optical sensor, which is then displayed during the medical intervention. Corresponding imaging systems are also provided.

Numerous advantages and benefits will become apparent to those of ordinary skill in the art upon reading the following detailed description of several embodiments. The invention may take form in various components and arrangements of components, and in various process operations and arrangements of process operations. The drawings are only for the purpose of illustrating many embodiments and are not to be construed as limiting the invention.

The present disclosure describes methods and systems for adaptive image guided medical interventions using an optical shape sensing of a patch affixed to the patient's body at an intervention insertion site and/or in proximity to the target anatomy of interest. The methods and systems may be used in conjunction with one or more imaging modalities, such as for example Computed Tomography (CT), Magnetic Resonance Imaging (MRI), ultrasound, fluoroscopy and the like.

Figure 1:
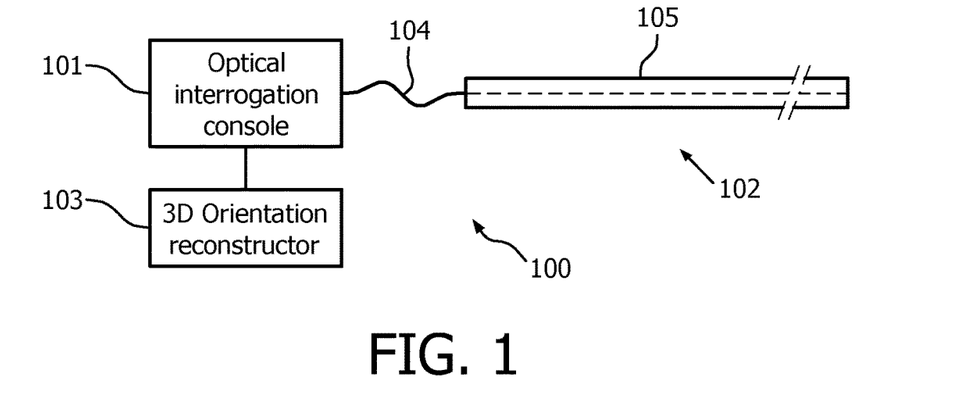
FIG. 1 schematically illustrates an optical sensing system 100, which monitors an orientation of an optical sensor device.

FIG. 1 schematically illustrates an optical sensing system 100. The optical sensing system 100 has an optical interrogation console 101 optically connected to at least one optical sensor device 102 and electronically connected to a three-dimensional orientation reconstructor 103. The optical interrogation console 101 sends an optical interrogation signal to an optical wire 104 which is embedded within or on a substrate material 105 to form the optical sensor device 102. The optical signal travels out to the optical sensor device 102 and is then reflected back through the wire 104, in a manner described further below, to the console 101. The reflected optical signal carries information which is indicative of some property of the optical sensor device 102. That information may include, for example, an orientation of the optical sensor device 102. The optical interrogation console 101 measures the reflected light, and electronically passes the measurements on to the three-dimensional orientation reconstructor 103 for analysis.

The three-dimensional orientation reconstructor 103 includes a processor and a memory for performing suitable calculations. Thus the functions described herein can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like. The Logic of the orientation reconstructor 103 may most easily be embodied as part of a medical intervention planning and execution software package.

The methods and systems described herein can be implemented on a variety of platforms including, for example, networked control systems and stand-alone control systems. Additionally, the logic shown and described herein preferably resides in or on a computer readable medium. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

Figure 2:
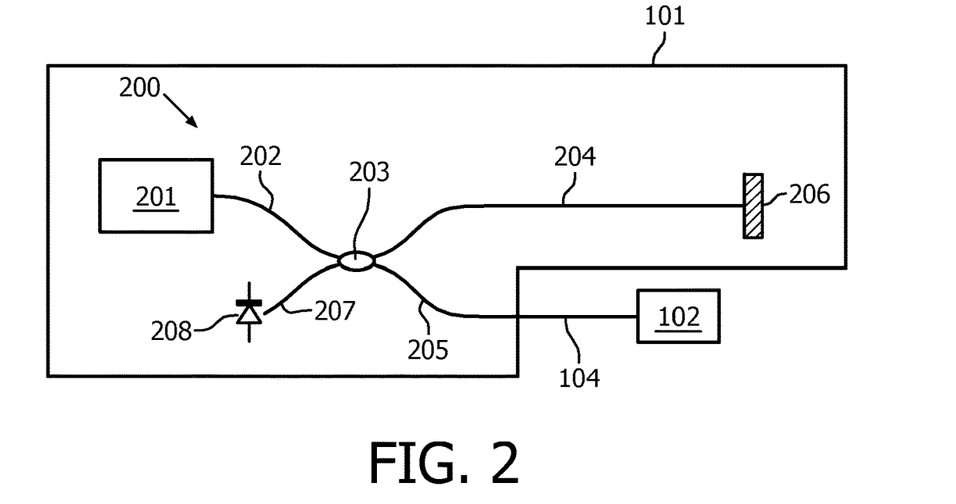
FIG. 2 schematically illustrates an optical Fourier domain reflectometer system 200 which may be used in conjunction with the optical sensing system 100.

The optical interrogation console 101 may be any device or system structurally configured for transmitting light to the optical wire 104 and receiving and measuring reflected light back from the optical wire 104. In one embodiment, the optical interrogation console 101 employs at least one optical Fourier frequency domain reflectometer and other appropriate electronics or devices as known in the art. The principles of such a reflectometer 200 are illustrated in FIG. 2. Other suitable optical interrogation console 101 setups are known and can be used in the optical sensing system 100.

The reflectometer system 200 has a tunable light source 201 with a coherent light output 202 which may be tuned to have a desired wavelength. The light output 202 of the light source 201 travels through a splitter 203 which splits the light signal 202 into a reference channel 204 and a sample channel 205. The light which enters the reference channel 204 travels to a mirror 206 to reflect back to the splitter 203 along the reference channel 204, which has a known and constant optical path length. The light which enters the sample channel 205 travels to the external optical wire 104, where it interacts with the optical sensor device 102 and is reflected back to the splitter 203 along the same path 104 and 205. The combined optical path length of the sample channel 205 and the external optical wire 104 is a known constant.

The two optical signals reflected back to the splitter 203 are then combined into a measurement optical signal 207 by the splitter 203 and directed to a photo detector 208. The photo detector 208 records the measurement optical signal 207. By varying the light output 202 properties in a known and controlled manner, and recording the resulting measurement optical signals 207 as the light output 202 is varied, the reflectometer system 200 creates an interference pattern. The interference pattern is indicative of at least an orientation of the optical sensor device 102. The optical interrogation console 101 measures the interference pattern, and electronically sends the recorded information to the three-dimensional orientation reconstructor 103 for analysis.

Referring again to FIG. 1, the optical wire 104 may be any type of flexible material suitable for carrying the light signals to and from the optical sensor device 102. Suitable materials include, for example, flexible and optically transparent glass or plastic materials. Other suitable materials may be used. The optical wire 104 may contain a single optical fiber core, or multiple optical fiber cores.

The substrate 105 may be any type of material suitable for embedding, carrying or otherwise supporting the optical wire 104. Suitable examples of appropriate substrates 105 include, but are not limited to, patches, deployable balloons such as rectal balloons, guidewires, needles, catheters, filters, baskets, helixes, endoscopes, and the like. The substrate 105 and/or the optical wire 104 supported by the substrate 105 may form a shape comprising one or more of an elongated straight shape, a curved line shape, a spiral shape, a ring shape, a loop shape, a helix shape, or any other shape. The material and shape of the substrate 105 may be changed to provide different results depending on the clinical application, for example by better fitting to a specific body part or tissue within the body. The specific substrate 105 may also be selected based on the type of tissue present where the optical sensor device 102 is to be inserted on or into a patient. In this way the optical wire 104 and the substrate 105 together form a flexible and configurable volume to obtain orientation information from the optical sensor device 102. However, in some embodiments, the optical sensor device 102 may comprise solely an optical wire 104, without any substrate 105.

The optical wire 104 can be used to obtain orientation information regarding the optical sensor device 102 using fiber optic tracking technology, as discussed above. This is done by optically interrogating one or more orientation fiber cores within the optical wire 104. In a first embodiment, for example, the orientation fiber core(s) each incorporate an array of Bragg gratings integrated along a length of the optical wire 104 as known in the art. In a second embodiment, as another example, the orientation fiber core(s) each have natural variations in optic refractive index occurring along the length of the wire as known in the art, such as a Rayleigh scattering based optical fiber core. Other fiber optic orientation tracking devices or structures may alternatively or additionally be used.

The interference patterns created by the light reflected from such structures in the orientation fiber core(s) of the optical wire 104 are recorded by the optical interrogation console 101 and passed on to the three-dimensional orientation reconstructor 103. The three-dimensional orientation reconstructor 103 is broadly defined herein as any device or system structurally configured for translating measured reflection spectra data received from the orientation fiber core(s) of the optical wire 104 into a three-dimensional orientation of the optical sensor device 102. For example, an axial reflectivity profile (A-line) of the optical sensor device 102 may be obtained by discrete Fourier transform (DFT) of the sampled signals. Also, in some embodiments, the sampled signals may be combined with one or more biophysical models to derive the estimated orientation information.

In CT guided interventions, the optical sensing system 100 can be integrated within the gantry of the CT imaging system. In that way, the shape and position of the optical fiber core(s) 104 relative to the CT imaging scan plane can be monitored. That is, the optical shape sensing coordinate system is known relative to the CT imaging system coordinate frame of reference. For an optical fiber 104 connected to a medical instrument such as a biopsy needle or a radiofrequency ablation needle, the position relative to the CT data set is therefore known. Hence, navigation of the medical instrument based on the CT data is feasible.

Figure 3:
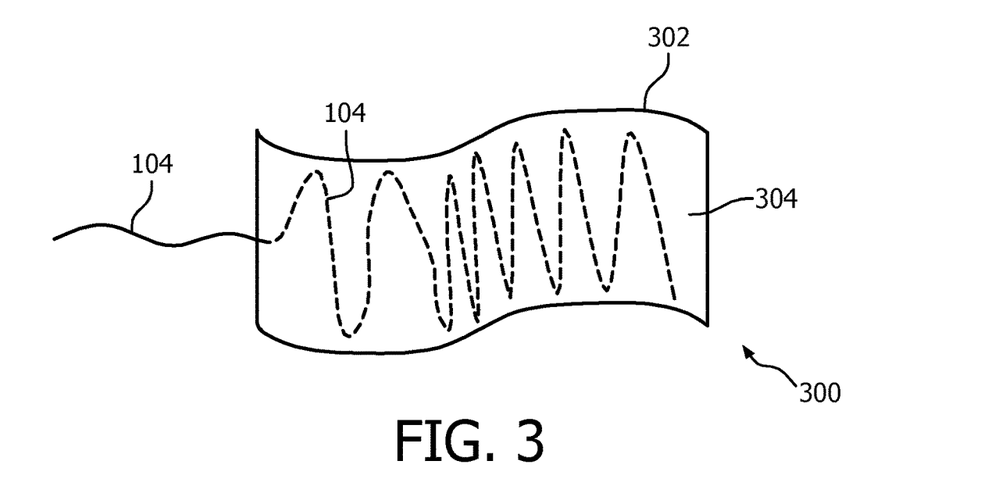
FIG. 3 schematically illustrates an optical sensor device in the form of a patch 300.

FIG. 3 illustrates a representative optical sensor device 102, in the form of a patch 300. The patch 300 includes a flexible substrate 302 which carries an optical wire 104 of an optical sensing system 100. The substrate 302 may be formed from any material which is flexible enough to conform to the external contour of a patient's body, and which does not pose any material health hazards to the patient. The substrate 302 may be created in any shape which is convenient for the particular application, including circular, square, rectangular, and the like. The substrate material 302 may be, for example, an x-ray or ultrasound transmissive cotton or fibrous material. An underside 304 of the patch 300 may be affixed to the patient's skin where the medical instrument is to be inserted during the intervention procedure, and/or in close proximity to the target anatomy of interest.

Attachment of the patch 300 on the patient's body may be accomplished in many ways. In one embodiment, an adhesive bonding material is applied to the underside 304 of the patch 300 in order to create a releasable adhesive bond with the patient's skin. Adhesives commonly used to attach ECG probes may be used for this purpose. In a second potential attachment, the substrate material 302 may be tightly wrapped around the patient's body and held in place, for example, by hook-and-loop structures, magnetic locking components, or mechanical clasps. In yet another potential embodiment, the patch 300 may be affixed to the patient's body by suction members. One of ordinary skill in the art will know of many other ways to attach the patch 300 on the patient's body.

The patch 300 may also be formed of multiple, separate components (not shown). For example, the substrate material of the patch 300 can comprise a matrix which adheres directly to the patient surface. Such a matrix substrate may be disposable, so that it can be discarded after one use. In that event, a re-usable component containing the optical fibers 104 can be reversibly attached to the disposable matrix to form the patch 300. This permits a single set of optical fiber(s) 104 to be used for multiple procedures, following sterilization if needed, which reduces the usage costs of the system.

The optical fiber 304 arrangement within the patch 300 can provide for designated fiber-free zones or ports in the patch 300 (not shown). These zones identify areas of the substrate 302 through which a needle or other medical instrument can penetrate without risk of damaging the optical fibers 304.

A single patch 300 can be combined with other patches 300, and/or with other optical shape sensor devices 102. For example, one or more external patches 300 may be combined with an internal sensor device 102 which is inserted into the patient along with a medical instrument during an intervention procedure.

The patch 300 is capable of accurately measuring the external surface deformation of the patient's body during insertion of the medical instrument. Consequently, the patch 300 can be used to generate a deformed CT roadmap image while the medical instrument is progressing towards the target within the patient. For example, a finite element model or other numerical model representing the tissue and subsequent deformation can be driven with the deformation observations from the patch surface 304, the medical instrument, and their measured interactions. In this way, more accurate intra-operative navigation is feasible, using lower imaging radiation dose levels.

The patch 300 may be attached to the patient's body during the first, pre-operative CT scan. In that event, the patch 300 can also be used to measure the breathing state in the target region during the intervention procedure. For example, if the pre-operative CT scan is acquired during breath hold, the determined shape and position of the patch 300 can be used during the intervention procedure to verify that the patient is in a comparable breathing state during insertion of the medical instrument. If a breathing gated pre-operative CT scan is acquired, the patch 300 may enable adaptive four-dimensional road mapping to improve the subsequent intervention procedure.

Figure 4A:
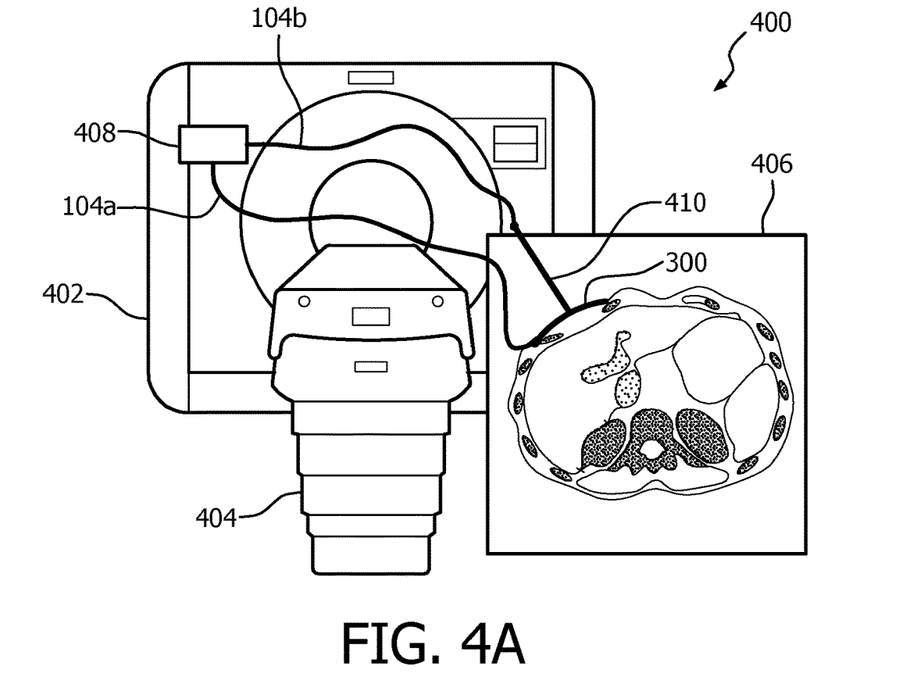
FIGS. 4A and 4B schematically illustrate a CT imaging system 400 incorporating the optical sensing system 100.
Figure 4B:
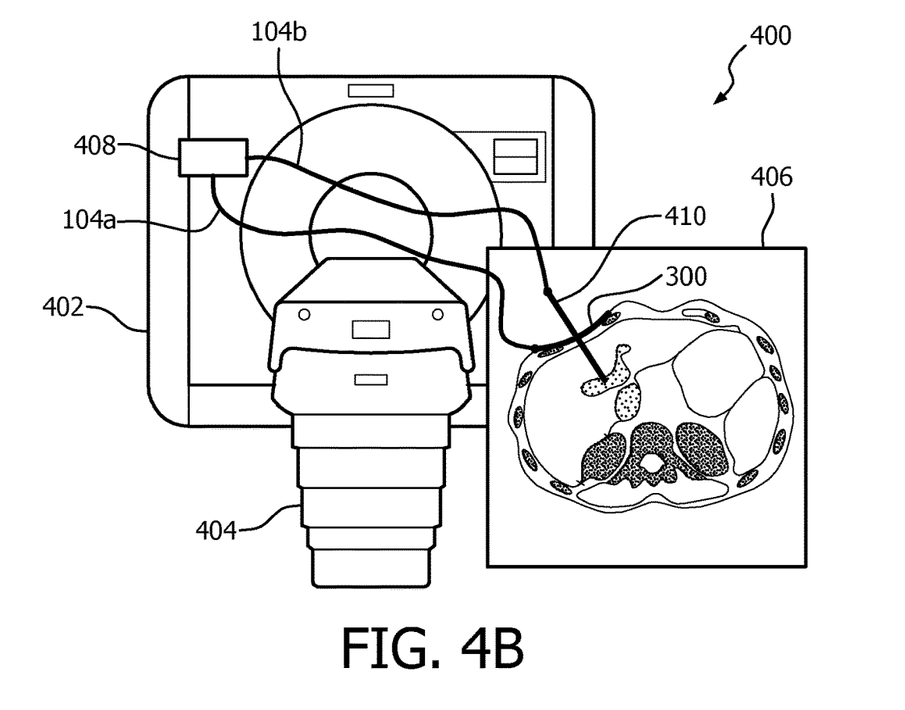

FIGS. 4A and 4B schematically illustrate a CT imaging system 400 which includes the optical sensing system 100. Thus, the CT imaging system 400 includes a gantry 402, a patient support table 404, and an associated display 406. The CT imaging system 400 further includes an optical sensing system such as the system 100 described above, which incorporates two optical sensor devices. Thus, one end of a first optical wire 104a is connected at 408 to an optical interrogation console 101 housed inside the gantry 402. The other, distal end of the first optical wire 104a is connected to a patch 300 which is disposed on the patient's body at the point of a needle 410 insertion. This is schematically reflected in FIGS. 4A and 4B, which show the wire 104a leading from the gantry 402 to the image of the patient on the display 406.

A second optical wire 104b is also connected to the optical interrogation console 101 housed inside the gantry 402 at 408. The second optical wire 104b follows the needle 410 as it is inserted into the patient's body during an intervention procedure. This is schematically reflected in FIGS. 4A and 4B, which show the wire 104b leading from the gantry 402 to the image of the patient on the display 406. The second optical wire 104b thus monitors the orientation of the needle 410 as it is inserted into the patient's body. The display 406 may show the orientation of one or both of the fibers 104a and 104b during the intervention procedure. Thus, the display 406 in FIG. 4A shows the orientation of the patch 300 and the needle 410 at the moment the needle 410 is inserted into the patient's body. The display in FIG. 4B shows the orientation of the patch 300 and the needle 410 at an intermediate point during the insertion.

Figure 5:
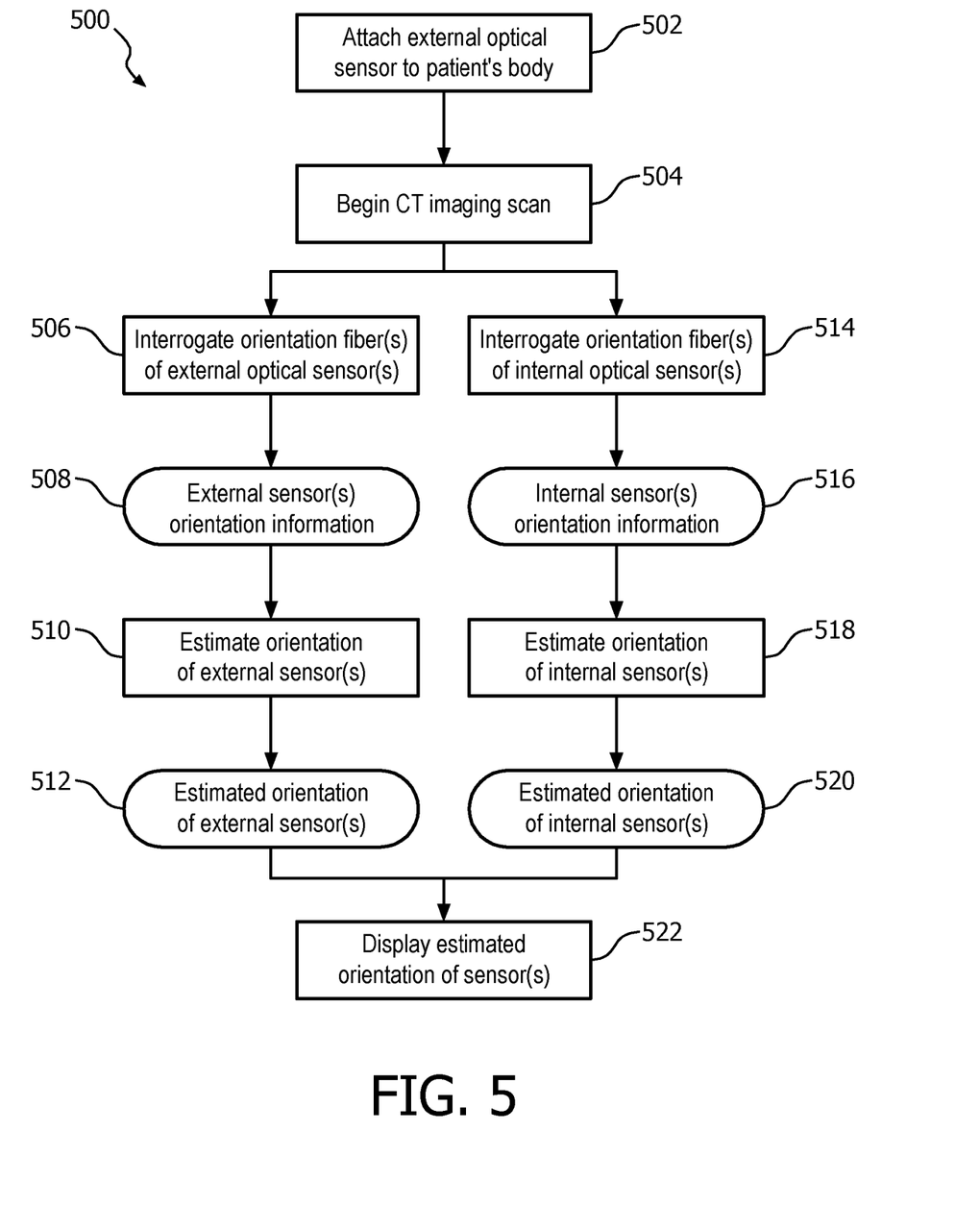
FIG. 5 illustrates steps of a method for using an optical sensing system during a medical intervention procedure.

In this way a method for using an optical sensing system 100 during a medical intervention procedure is provided. An exemplary such method 500 is illustrated in FIG. 5. In a first step 502, at least one external optical sensor patch 300 is attached to the patient's body at the medical instrument insertion site, and/or in close proximity to the target tissue of interest. Other optical sensor devices 102 may also be embedded on or within the patient's body during the intervention. The patient is then placed within an imaging system, such as the exemplary CT imaging system 400 discussed above. The imaging system 400 then begins to generate 504 images of the patient's body, and the medical intervention begins 504.

During the intervention procedure, the optical sensing system 100 is utilized to monitor 506 the orientation of the patch 300 on the patient's body. More specifically, the orientation fiber(s) in the optical wire 104 are interrogated 506 by the optical interrogation console 101 to obtain patch orientation information 508 during the intervention procedure. The patch orientation information 508 comprises measuring the light signals returning from the patch 300 as a function of the interrogation light properties. If the optical wire 104 contains multiple orientation fiber cores, this information 508 may be recorded separately for each core. The light reflection within the optical wire 104 of the patch 300 may be invoked for example by embedded periodical structures within the optical wire 104 (e.g., Fiber Bragg Gratings) or by non-periodic, random variations in the refractive index of the optical wire 104 (e.g., Rayleigh scattering).

The orientation information is provided to the three-dimensional orientation reconstructor 103, which uses the orientation information to estimate 510 an orientation 512 of the patch 300 on the outside surface of the patient's body. The three-dimensional shape reconstructor 103 may, for example, process the reflection spectra 508 to generate strain values at multiple positions along the orientation fiber core(s) of the optical wire 104. The strain sensors may comprise at least one of a Fiber Bragg Grating (FBG) and a Rayleigh scatter interrogation.

Optionally, the optical sensing system 100 may also be utilized during the intervention to monitor 514 an orientation of an internal optical sensor device which is inserted into the patient along with the medical instrument. More specifically, the orientation fiber(s) in the optical wire leading to the internal optical sensor device are interrogated 514 by the optical interrogation console 101 to obtain medical instrument orientation information 516 during the intervention procedure. The medical instrument orientation information 516 comprises measuring the light signals returning from the internal optical sensor as a function of the interrogation light properties. The medical instrument orientation information 516 is provided to the three-dimensional orientation reconstructor 103, which uses the orientation information to estimate 518 an orientation 520 of the medical instrument within the patient.

The optical wires may in some embodiments advantageously include an area of higher sensitivity by including an area with a higher number of optical fibers having optical strain sensors. For example, the optical wires may have a first area where a first number of optical fibers having optical strain sensors are present, and a second area where a second number of optical fibers having optical strain sensors are present. In this way the second area will have a higher sensitivity than the first area. The higher sensitivity may help achieve a better resolution regarding the orientation of the optical wires. As one example, the first area may have one optical fiber and a first sensitivity, and the second area may have four optical fibers and a second sensitivity which is higher than the first sensitivity. The three-dimensional shape reconstructor 103 combines the strain values to generate a three-dimensional reconstruction of the shape and position of the optical wires. For example, the strain measurements may be converted to rotation angles and the associated rotation matrices may be used to update a tangent vector, a normal vector and a binormal vector (i.e. columns of a Jacobian matrix).

The external sensor estimated orientation 512 and the internal sensor estimated orientation 520 (if measured) are transmitted to the CT imaging system 400 processor during the intervention procedure. The CT imaging system 400 registers the coordinate systems of the estimates 512 and 520 with the coordinate system of the CT imaging system 400. It then uses the estimated information 512 and 520 to display 522 an orientation of the external sensor and the internal sensor on or within the patient's body on a display 406 of the CT imaging system 400, during the intervention procedure. In some embodiments, the sensors may not themselves be shown on the display 406. Instead, the display 406 may simply show the orientation of the patient's skin surface (based on the external sensor information) and the medical instrument within the patient's body (based on the internal sensor information).

In yet additional embodiments, the CT imaging system 400 may use the patch orientation information 510 to provide a notification to a user of the system. The user notification may take many forms. In one embodiment, the system may simply notify the user that the patch deformation has exceeded pre-set thresholds, indicating something may have gone wrong during the intervention. In another embodiment, the system 400 may additionally present the user with a proposed modification of the intervention procedure in order to account for changes in circumstances.

As already described above, the CT imaging system 400 may reconstruct gathered imaging data in order to form a three-dimensional image volume for showing on the display 406 of the system. The CT imaging system 400 may additionally include one or more user input devices (not shown) which allow a user to interact with and control the operation of the system 400. For example, the user may configure appropriate views of the image data for displaying on the display 406, such as for example a two-dimensional imaging slice which contains the medical instrument insertion path (e.g. FIGS. 4A and 4B), or a bull's-eye view of the medical instrument insertion path.

The invention has been described with reference to the several embodiments. Obviously, modifications and alterations will occur to others upon reading and understanding the preceding detailed description. For example, visual feedback for steering the medical instrument during the intervention may be provided. It is intended that the invention be construed as including all such modifications and alterations insofar as they come within the scope of the appended claims or the equivalents thereof. The invention may take form in various compositions, components and arrangements, combinations and sub-combinations of the elements of the disclosed embodiments.

Having thus described several embodiments, the invention is now claimed to be:

1. A method for generating imaging data during a medical intervention performed on a patient, the method comprising:
   providing an external optical sensor adapted to be attached to the patient, the external optical sensor comprising at least one orientation fiber core configured to deform due to insertion of a medical intervention instrument through the external optical sensor during the medical intervention when attached to the patient and configured to measure a three-dimensional orientation of the external optical sensor relative to a point of reference;
   optically interrogating the external optical sensor to generate external optical sensor three-dimensional orientation information regarding the external optical sensor during the medical intervention, and using the external optical sensor three-dimensional orientation information to estimate a three-dimensional deformation of the external optical sensor during the medical intervention; and
   displaying deformation of the patient due to insertion of the medical intervention instrument using, at least in part, the external optical sensor three-dimensional deformation estimate;
   wherein the external optical sensor comprises a patch including a substrate supporting the at least one orientation fiber core, and wherein the substrate comprises at least one zone which does not contain any orientation fiber cores, such that the medical intervention instrument is inserted through the at least one zone; and
   wherein the insertion through the at least one zone comprises penetrating the substrate with the medical intervention instrument.

2. The method of claim 1, wherein the optical interrogation step is performed using an optical Fourier frequency domain reflectometer.

3. The method of claim 1, further comprising:
   inserting an internal optical sensor associated with the medical intervention instrument into the patient, the internal optical sensor comprising at least one orientation fiber core configured to measure a three-dimensional orientation of the internal optical sensor relative to the point of reference;
   optically interrogating the internal optical sensor to generate internal optical sensor three-dimensional orientation information regarding the internal optical sensor during the medical intervention, and using the internal optical sensor three-dimensional orientation information to estimate the three-dimensional orientation of the internal optical sensor during the medical intervention; and
   displaying an orientation of the medical intervention instrument using, at least in part, the internal optical sensor three-dimensional orientation estimate.

4. The method of claim 1, wherein the at least one orientation fiber core comprises at least one of an array of Bragg gratings and a Rayleigh scattering structure.

5. The method of claim 1, further comprising:
   attaching the external optical sensor on the patient before performing a pre-operative imaging scan;
   optically interrogating the external optical sensor during the pre-operative imaging scan to measure a first breathing state of the patient;
   optically interrogating the external optical sensor during the medical intervention to measure a second breathing state of the patient, and
   comparing the first breathing state with the second breathing state.

6. The method of claim 1, further comprising generating a model representing the deformation of the patient based on the external optical sensor three-dimensional deformation estimate.

7. The method of claim 1, further comprising notifying a user that the deformation of the patient has exceeded a deformation threshold.

8. The method of claim 1, further comprising presenting a user with a proposed modification to the medical intervention being performed on the patient based on the external optical sensor three-dimensional deformation estimate.

9. The method of claim 1, further comprising generating an image representing deformation of a surface of the patient during the medical intervention based on the external optical sensor three-dimensional deformation estimate and a pre-operative imaging scan.

10. The method of claim 1, wherein the patch comprises an identification of the at least one zone which does not contain any orientation fiber cores.

11. A non-transitory computer-readable medium having one or more executable instructions stored thereon which, when executed by at least one processor, cause the at least one processor to perform a method for generating imaging data during a medical intervention performed on a patient, the method comprising:
    optically interrogating an external optical sensor configured to be attached to the patient, the external optical sensor comprising at least one orientation fiber core configured to deform due to insertion of a medical intervention instrument through the external optical sensor during the medical intervention when attached to the patient and configured to measure a three-dimensional orientation of the external optical sensor relative to a point of reference;
    in response to the optically interrogating the external optical sensor, generating external optical sensor three-dimensional orientation information regarding the external optical sensor during the medical intervention, and using the external optical sensor three-dimensional orientation information to estimate a three-dimensional deformation of the external optical sensor during the medical intervention; and displaying deformation of the patient due to insertion of the medical intervention instrument using, at least in part, the external optical sensor three-dimensional deformation estimate;

wherein the external optical sensor comprises a patch including a substrate supporting the at least one orientation fiber core, and wherein the substrate comprises at least one zone which does not contain any orientation fiber cores, such that the medical intervention instrument is inserted through the at least one zone; and wherein the insertion through the at least one zone comprises penetrating the substrate with the medical intervention instrument.

* * * * *